United States Patent [19]

Hagler

[11] Patent Number: 4,672,797
[45] Date of Patent: Jun. 16, 1987

[54] METHOD AND APPARATUS FOR SECURING AND TRANSFERRING GRID SPECIMENS

[75] Inventor: Herbert K. Hagler, Dallas, Tex.

[73] Assignee: Gatan, Inc., Pleasanton, Calif.

[21] Appl. No.: 747,255

[22] Filed: Jun. 21, 1985

[51] Int. Cl.⁴ .......................... B65B 5/04; B65B 7/26; B65B 67/02

[52] U.S. Cl. ...................................... 53/467; 53/377; 53/390

[58] Field of Search ................. 53/467, 468, 471, 484, 53/485, 491, 440, 376, 377, 390, 127

[56] References Cited

U.S. PATENT DOCUMENTS

| | | | |
|---|---|---|---|
| 679,811 | 8/1901 | Williams | 53/377 X |
| 3,562,997 | 2/1971 | Pearl et al. | 53/377 X |
| 3,866,393 | 2/1975 | Warner et al. | 53/377 X |
| 4,586,316 | 5/1986 | Backman et al. | 53/467 X |

OTHER PUBLICATIONS

D. Parsons, D. J. Bellotti, W. W. Schulz, M. Buja and H. K. Hagler, "Towards Routine Cryoultramicrotomy" (1984).

H. K. Hagler & L. M. Buja, "New Techniques for the Preparation of Thin Freeze Dried Cryosections for X-Ray Microanalysis" *Science of Biological Specimen Preparation* (pp. 161-166).

*Primary Examiner*—Horace M. Culver
*Attorney, Agent, or Firm*—Jerry W. Mills; Jefferson Perkins

[57] ABSTRACT

An apparatus (10) for use in securing a specimen (S) in a folding specimen holder (58) having an arm blade (12). A spring clip (26) releasably secures the grid (58) to the arm blade (12) so that one or more specimens may be loaded into the holder (58). A slider (22) mounted on the arm blade (12) operates to fold the holder (58) upon itself in order to secure the specimens (S) in the holder (58). The spring clip (26) is thereafter operated to release the holder (58) after the holder (58) has been transferred from a first workstation (48) to a second workstation (62).

22 Claims, 9 Drawing Figures

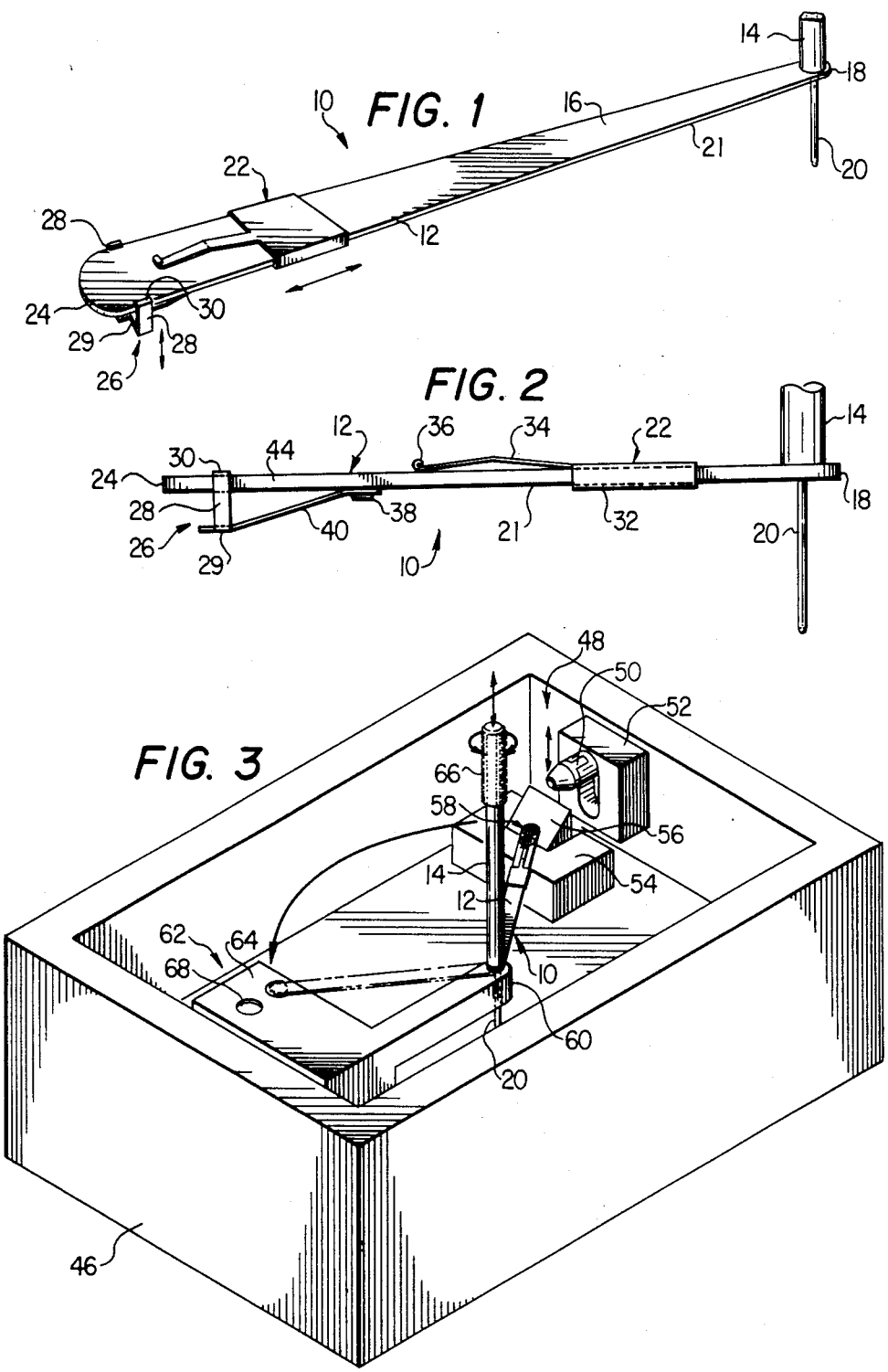

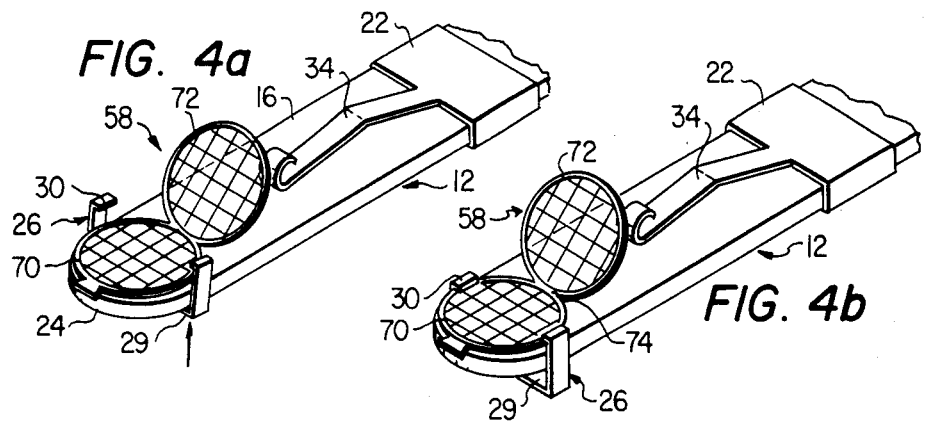
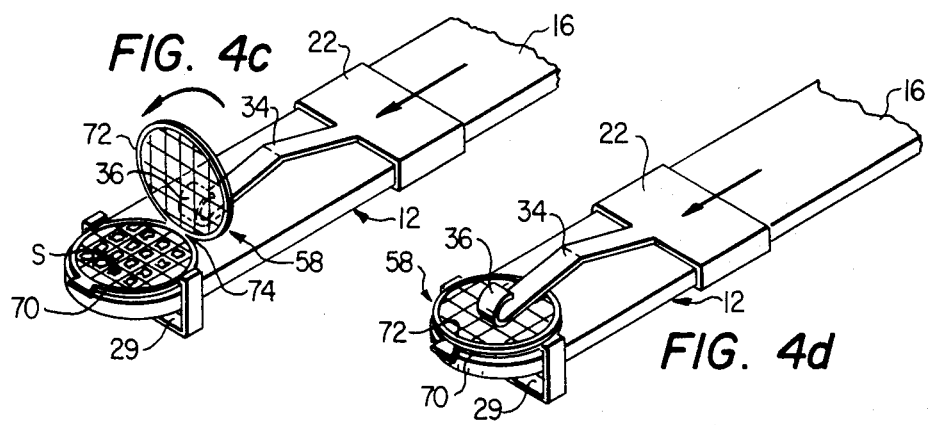
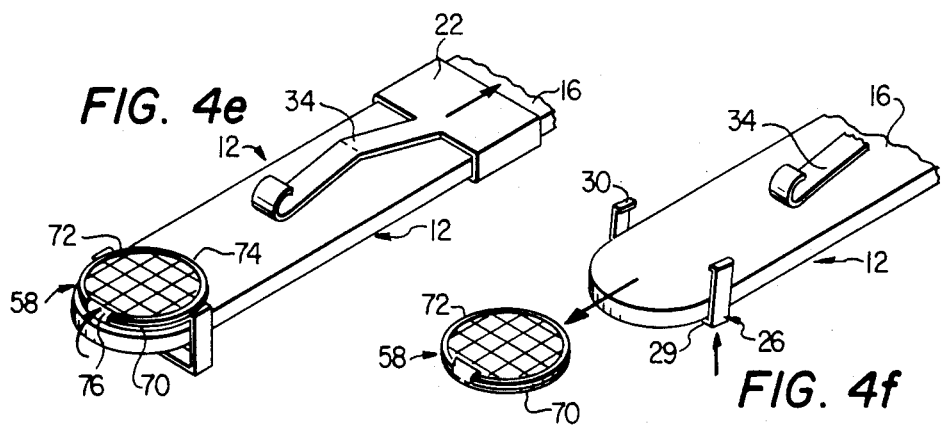

METHOD AND APPARATUS FOR SECURING AND TRANSFERRING GRID SPECIMENS

TECHNICAL FIELD OF THE INVENTION

This invention relates generally to the field of preparing and processing specimens as for microscopy and particularly relates to a method and apparatus for both securing a grid and transferring it between workstations.

BACKGROUND OF THE INVENTION

Small biological specimens are prepared for examination under the electron microscope by placing them on a reticulate specimen grid. Specimen grids are used particularly in the field of Cryoultramicrotomy, where specimens are examined at extreme high power under supercooled ($-196°$ C.) conditions.

Conventional specimen preparation practices for Cryoultramicrotomy are illustrated by the following articles: D. Parsons, D. J. Bellotto, W. W. Schulz, M. Buja and H. K. Hagler, "Towards Routine Cryoultramicrotomy", and H. K. Hagler and L. M. Buja, "New Techniques for the Preparation of Thin Freeze Dried Cryosections For X-Ray Microanalysis", Science of Biological Specimen Preparation, pp. 161–166, both available from H. K. Hagler, University of Texas, Department of Pathology, Health Science Center at Dallas, 5323 Harry Hines Blvd., Dallas, Tex. 75235.

In conventional practice, a grid on which the microscope specimens will be mounted is coated with a formvar solution that dries to form a transparent film across the grid. The grid is then chilled to $-130°$ C. by placing it within a block inside of a cryochamber. The cryochamber is conventionally made out of stryofoam and is filled with gaseous nitrogen at $-130°$ C. Inside the cryochamber, a grid transfer arm is provided in order to move the specimen grid (which is preferably a 50 to 400 mesh copper grid) from one location to another. The transfer arm conventionally has a pair of forceps on one of its ends in order to grip the grid. At a first location, sections of tissue are placed on the grid and the transfer arm then moves the grid over to a second location. During transfer, the specimens on the open, single grid are subject to being inadvertently jarred from their ideal locations or even swept off the grid.

The grid is then placed in a formvar-coated beryllium capsule in order to retain the specimens between two films of formvar. The capsule is assembled and loaded into a coldstage, which is used to protect the cold specimen as it is transferred to the electron microscope.

Recently, a holder comprising two grids hinged to each other has been used for containing tissue specimens. Both copper mesh parts of the double grid are coated with formvar, the tissue specimens are placed on the grid and the double grid is manually folded upon itself. The use of a double grid obviates the need for an expensive beryllium capsule, as the grid itself retains the specimen between two transparent formvar films. It also protects the specimens in transfer between workstations in the cryochamber.

However, the conventional forceps and grid transfer arm are less than ideal for the transfer of the double grid from one location to another. In conventional practice, the arm forceps must grip the lower grid of the double grid, and the upper grid must be folded onto the lower grid by using a pre-cooled second pair of manual forceps. After the upper grid has been folded onto the lower grid, one of the transfer arm forceps will be wedged between the upper grid and the lower grid. The arm grid must thus be subsequently disengaged by opening the transfer arm forceps and removing the grid with another pair of manual forceps.

Either of the steps of manually folding the grid over onto the loaded lower grid or extracting the transfer arm forceps from the folded grid may disturb the location of the specimens, as these manual functions can be controlled only to the extent permitted by the motor skills of the operator.

Thus, a need has arisen for a grid securement and transfer arm which will provide a more automatic grid folding function and make the task of transferring the specimen grid from a first location to a second location surer and easier.

SUMMARY OF THE INVENTION

The present invention provides a new method and apparatus for securing a tissue specimen in a folding specimen holder. A specimen holder is provided in an open position, and the holder is releasably secured to a transfer arm having a holder folding device. The specimen is loaded into the holder, and the holder is folded on itself with the aid of the folding device. The transfer arm transfers the grid from a first workstation to a second workstation and releases the holder from the transfer arm.

In a preferred embodiment, a specimen grid is secured to an upper surface of the transfer arm by means of a spring clip. The spring clip is spring-biased against the upper surface of the transfer arm. In order to release the clip to allow the admittance of a specimen grid, the operator presses downward on the transfer arm on a workstation block, pushing the spring clip upward in relation to the transfer arm. The lower portion of the double grid is then placed on the upper surface beneath the clip, and the operator raises the transfer arm to secure the lower grid between the clip and the upper surface. The specimens are then secured into the grid with the use of a slidable folding device at a first workstation. The grid is transferred to a second workstation and the operator presses the arm down on a block in order to release the folded specimen grid from the transfer arm.

BRIEF DESCRIPTION OF THE DRAWINGS

For a more complete understanding of the present invention and the advantages thereof, reference is now made to the following description taken in conjunction with the accompanying Drawings in which:

FIG. 1 is a perspective view of the grid transfer arm of the invention;

FIG. 2 is a partial elevation of the grid transfer arm shown in FIG. 1, illustrating the spring clip and the slider mechanism of the invention;

FIG. 3 is a perspective view of a cryobox employing the specimen grid transfer arm of the invention, showing an alternate location of the grid transfer arm in phantom; and FIGS. 4a–4f are perspective views of the free end of the transfer arm shown in FIG. 1, showing various steps in the grid securing and transferring process.

DETAILED DESCRIPTION OF THE INVENTION

Referring to FIG. 1, the transfer arm 10 of the present invention has an arm blade 12 that is preferably fabricated of a metal such as stainless steel. For the illustrated application, arm blade 12 is conveniently sized to be about 75 millimeters long. An upstanding handle 14 is affixed to an upper surface 16 of blade 12 at a pivot end 18 thereof. A pivot 20 is affixed to a lower arm surface 21 at end 18 and extends downwardly from arm blade 12. Pivot 20 is preferably coaxial with handle 14. A sliding grid folder or slider 22 is slidably mounted on arm blade 12 and is movable toward a free end 24 of arm 12 or toward pivot end 18. Slider 22 can be fashioned of stainless steel.

A spring clip 26 is mounted on arm blade 12. Spring clip 26 includes upstanding side portions 28 joined by a bottom member 29. Clip portions 30 extend inwardly from the top of side portions 28 and, when spring clip 26 is empty, are spring loaded against upper surface 16. For ultramicrotomic work, the distance between inwardly extending clip portions 30 should be about from 1.9 to 2.5 millimeters in order to be correctly sized to receive the specimen grid (later shown).

Referring to FIG. 2, an elevation of transfer arm 10 shows the relationship of upstanding handle 14 and depending pivot 20 to arm blade 12. Pivot 20 is affixed as by welding to lower surface 21. Blade 12 forms a slight downward angle from the handle pivot axis in order to aid the pressing action of blade 12 on a block (later described).

Slider 22 has side portions 32 (only one shown) which extend over the edges of blade arm 12 from upper surface 16 and fold inwardly to parallel lower surface 21. The fitting of slider 22 to blade arm 12 is loose enough to allow movement of slider 22 toward and away from end 24 when operated by a pair of forceps or the like. Slider 22 includes a push arm 34 that extends forwardly on upper surface 16 toward end 24. Push arm 34 ends in an upstanding contact member 36 to provide a pushing surface for contacting a grid. Preferably, push arm 34 is slightly sprung toward upper surface 16 in order to slightly tension slider 22 against blade arm 12 so that contact member 36 may be pushed forward in a low position.

Spring clip 26 includes a spring 40 which is attached as by welding to lower surface 21 at a point 38. Bottom member 29, shown in FIG. 2 in phantom and better shown in FIGS. 4b-4e, extends laterally from spring member 40 at least as far as the width of arm blade 12. Side portions 28 extend upwardly from the ends of bottom member 29 past sides 44 (one shown) of arm blade 12. Clip 26 may be integrally formed from a sheet of stainless steel, or may be formed of several stainless steel elements welded together. Alternately, clip 26 may be fabricated of tungsten wire, in which case clip members 30, bottom 29 and spring member 40 would be formed of wire segments instead of the flat sheet segments shown.

Push arm 34 is long enough to extend approximately to the position of side portions 28 from a position behind attachment point 38. This prevents any possibility of physical interference between spring member 40 and slider side members 32. Slider 22, spring clip 26 and arm blade 12 may be fabricated of other materials such as other metals, so long as they can withstand a −130° C. environment. For other uses outside of cold environments entailing the handling of larger specimens, transfer arm 10 could be formed of plastics.

FIG. 3 shows the positioning of transfer arm 10 inside a cryobox 46. The interior of cryobox 46 is filled with nitrogen gas at −130° C. in order to keep the biological specimens well frozen. Cryobox 46 commonly has a lid (not shown). At a first location or workstation 48 in box 46, a frozen biological specimen has been secured in a Tormey vise 50. Vise 50 is mounted in a guide block 52 and is movable in a vertical direction. A block 54 has an associated knife edge 56. The biological specimen (not shown) is mounted in the end of the Tormey vice 50, and sections of it are made by drawing the Tormey vice 50 downward past knife edge 56. Individual grid specimens are thereby formed on knife edge 56 and are subsequently transferred to a specimen grid 58 on arm blade 12.

Pivot 20 fits within a receptacle 60. Handle 14 may be rotated in order to rotate arm blade 12 from location 48 to a second location or workstation 62. It also may be raised up and down in order to raise or depress arm blade 12. At workstation 62, further processing of the specimen grid is performed. A block 64 is provided at second location 62. Handle 14 may be provided with a frictional surface 66 to provide a better manual grip.

Transfer arm 10 may be employed in other situations where it is desirable to transfer a small specimen in a holder from a first location to a second location. Arm 10 could be used in situations requiring the transfer of a specimen grid among three or more locations, instead of just two locations shown in the illustrated embodiment.

FIGS. 4a-4f illustrate sequential steps of the method of securing biological specimens in the double grid 58, and subsequently transferring the specimens from first location 48 to second location 62. In FIG. 4a, arm 12 is located at location 62 in FIG. 3. Bottom 29 of spring clip 26 is pressed upwardly in order to space clip members 30 from upper surface 16. Preferably, this is done by the operator pressing downward on handle 14, causing arm blade 12 to press downwardly on second location block 64. Spring clip 26 could also be manually squeezed upwardly toward blade 12 by a pair of forceps. Pressing blade arm 12 down on block 64 causes contact to be made between block 64 and bottom 29, pressing spring clip 26 upward against the spring force exerted by spring member 40 (FIG. 2). This spaces clip members 30 from upper surface 16. Blade 12 is made thick enough to substantially withstand any bending deformation. Alternately, blade 12 could be reinforced with upstanding or depending rib or channel members. In the illustrated embodiment, blade 12 is slanted slightly downward in order to compensate for any upward bending that does occur when blade 12 is pressed downwardly on block 64.

The double grid 58 shown is made out of number 50 copper mesh, lightly coated with carbon and coated with a formvar film. Grid 58 could be any mesh from 50 to 400 mesh. Another transparent plastic film such as Parlodian could be employed in the place of formvar. Grid 58 is generally sized between 2 mm and slightly over 3 mm for microscope applicatons. Grid 58 is retrieved from storage where it has been cooled to approximately −130° C. This storage can be provided by a suitable receptacle (not shown) in block 64 or elsewhere in cryobox 46 in order to protect it from any warming currents.

A lower grid portion 70 of double grid 58 is inserted between upper surface 16 and clip members 30 by means such as pre-cooled forceps or vacuum forceps. Grid 58 is originally provided in an open, unfolded position, with lower grid 70 being angularly separated from an upper grid portion 72.

In FIG. 4b, the operator has raised handle 14, releasing clip members 30 to exert spring force downwardly in the direction of the upper surface 16. Clip members 30 then grip lower grid 70 between themselves and upper surface 16. An upper grid 72 is hinged to an end of lower grid 70 by a hinge 74. Double grid 58 should be oriented on arm blade 12 such that hinge 74 is located about 90° from clip portions 30. In this way, upper grid 72 may be folded down onto lower grid portion 70 without interference from clip members 30. After grid 58 has been secured to arm 10, arm 10 is rotated from workstation 62 to workstation 48 (FIG. 3).

Referring to FIG. 4c, specimens S are removed from knife edge 56 (FIG. 3) and are loaded onto lower grid 70 with the aid of a hair (not shown). Each specimen is preferably entered on a separate interstice. A formvar coating forms a transparent film across the interstices to support specimens S.

After specimens S have been loaded onto lower grid 70, slider 22 is moved forwardly with forceps. Using the forceps to slide slider 22 forward is much easier than using the forceps to fold over upper grid 72. All manual movement is channeled by slider 22 in the desired forward direction, reducing the possibility that specimens S will be misaligned or even knocked off through hand-eye coordination error. As slider 22 moves forward, contact member 36 contacts upper grid 72 and pushes it forward to fold over on lower grid 70. The folding takes place at hinge 74.

FIG. 4d shows the completion of the folding of upper grid 72 onto lower grid 70. Like lower grid 70, upper grid 72 is coated with formvar to form a transparent film in between the interstices of its copper mesh. Therefore, specimens S are not completely enclosed in a transparent formvar film and are secured within double grid 58. Clip members 30 are now between upper grid 72 and lower grid 70 at locations spaced about 90° from hinge 74. In this position, double grid 58 can later be disengaged from clip members 30 by sliding grid 58 horizontally toward end 24.

In FIG. 4e, slider 22 is shown to be withdrawn, which can again be accomplished with the aid of precooled forceps. Grid 58 may be provided with a locking tab 76, which is preferably hinged to lower grid 70 at a point opposite hinge 74. If tab 76 is provided, it is folded upwardly with the aid of forceps over upper grid 72 in order to lock upper grid 72 to lower grid 70. Upper grid 72 and lower grid 70 will tend to bow slightly around clip members 30.

Locked grid 58 is now ready for transport between workstation 48 back to workstation 62. The invention provides an advantage over the conventional, single-grid method, as specimens S are secured in between two formvar surfaces during their transfer from one location to another. Previously, specimens S were often merely deposited on a plate, and thus were subject to being inadvertently swept off the grid surface.

In FIG. 4f, arm blade 12 has arrived back at workstation 62. The operator preferably presses down on handle 14 in order to exert upward pressure on bottom 29 of spring clip 26. Up to this point, inwardly extending clip portions 30 have been situated between lower grid 70 and upper grid 72. By using forceps, grid 58 is removed in a forward, horizontal direction, so that clip portions 30 merely slide out from between upper grid 72 and lower grid 70. Grid 58 is then further processed or may be protectively stored in block 64 by placement in a cold storage cylinder 68 (FIG. 3.)

The illustrated embodiment shows the invention as employed in a cryobox for securing and transferring grid specimens during preparation of the specimens for ultramicrotomy. However, the invention may also be employed in any situation where very small specimens are required to be secured in a hinged holder and then transferred from one location to the next. The invention may be employed with special advantage where the operating environment surrounding the specimen is different from the ambient environment. Thus, the present invention could be employed in a chamber having an evacuated atmosphere, or within a "hotbox" in which a radioactive shield means has to be erected between the specimens and the operator. The means to operate the apparatus of the invention may either be by hand and forceps as in the illustrated embodiment, or also could be by mechanical means.

In summary, the present invention provides a small specimen securement and transfer means which is easier to manipulate than the specimen securement and transfer means of the prior art. The invention provides a means to fold a specimen holder over onto itself, thus securing the specimens during their transfer from one workstation to another. A clip means secures the specimen holder during loading the holder and during transfer.

Although the preferred embodiment of the invention has been described in detail, it should be understood that various changes, substitutions and alterations can be made therein without departing from the spirit and the scope of the invention as defined by the appended claims.

What is claimed is:

1. A method for transferring a specimen contained in a holder from a first workstation to a second workstation, comprising:
   spring loading a spring clip mounted on a transfer arm against an upper surface of the transfer arm;
   pressing the transfer arm downwardly on a block in order to force the spring clip away from the upper surface;
   placing a first portion of the holder between the spring clip and the upper surface;
   releasing downward pressure on the transfer arm such that the spring clip secures the first portion to the upper surface;
   depositing a specimen on the first portion of the holder at the first workstation;
   folding a second portion of the holder over the first portion to close the holder over the specimen;
   moving the transfer arm from the first workstation to the second workstation; and
   releasing the holder from the transfer arm.

2. The method of claim 1 and including the step of pressing the spring clip upwardly in order to release the specimen holder from the arm at the second workstation.

3. The method of claim 2, wherein the spring clip is pressed against a second block at the second workstation in order to release the specimen holder.

4. The method of claim 3, wherein the transfer arm is movable in a vertical direction, the transfer arm being pressed downwardly on the second workstation block in order to press the spring clip upwardly.

5. The method of claim 1, wherein the transfer arm pivots from the first workstation to the second workstation.

6. The method of claim 1, wherein a folder is associated with the transfer arm, the method including the steps of:
  moving the folder toward the second portion of the holder until the folder makes contact with the second portion;
  pushing the folder against the second portion in order to fold the second portion over the first portion to close the holder; and
  withdrawing the folder.

7. A method for transferring a small specimen in a holder from a first workstation to a second workstation, the holder comprising a double grid having a lower grid and an upper grid, the method including the steps of:
  releasably securing the lower grid to an upper surface of a transfer arm with a spring clip;
  depositing a specimen on the lower grid at the first workstation;
  folding the upper grid over onto the lower grid using a folder;
  folding a catch hinged to the lower grid over the upper grid to lock the upper grid in place;
  moving the grid from the first workstation to a second workstation; and
  pressing the spring clip to release the double grid from the transfer arm.

8. The method of claim 7, wherein the spring clip has a bottom situated below a lower surface of the transfer arm, the bottom being connected to the lower surface by a spring element, the spring clip further including upstanding clip portions spring loaded against the transfer arm upper surface, the method including the steps of:
  pressing the bottom upwardly in order to space the clipped portions from the upper surface;
  inserting the lower grid between the upper surface and the clip portions; and
  releasing the bottom in order to secure the lower grid between the upper surface and the clip portions.

9. The method of claim 8, and further including the step of pressing the bottom upwardly after the grid has been moved to the second workstation in order to release the double grid.

10. The method of claim 9, wherein the bottom is pressed against a second workstation block by the transfer arm in order to release the double grid.

11. The method of claim 10, wherein the bottom is pressed against the second workstation block in order to space the upstanding clip portions upwardly from the upper surface.

12. The method of claim 11, wherein the transfer arm is mounted on a pivot and is movable in a vertical direction, the method including the steps of:
  pressing the transfer arm down on the second workstation block in order to space the clip portions upwardly from the upper surface;
  raising the transfer arm above the second workstation block using an upstanding handle mounted on the transfer arm in order to release the spring clip, securing the grid between the clip portions and the upper surface;
  rotating the transfer arm from the second workstation to the first workstation;
  rotating the transfer arm from the first workstation to the second workstation after the specimens have been secured in the grid; and
  pressing the transfer arm down on the second workstation block in order to release the grid from the transfer arm.

13. The method of claim 7, wherein the folder is slidably mounted on the arm, the step of folding the upper grid onto the lower grid including the steps of:
  sliding the folder forwardly until the folder contacts the upper grid;
  pushing the second grid with the folder so that the second grid folds over onto the first grid to assume its closed position; and
  slidably retracting the folder from the grids.

14. Apparatus for securing a specimen in a specimen holder having a first portion and a second portion foldable on the first portion to secure said specimen in the holder, the apparatus comprising:
  an arm;
  means for releasably securing the holder on said arm in order that the specimen may be loaded into the holder;
  a slider slidably mounted on said arm and slidable between a position remote from the holder to a position proximate the holder, said slider operable to be advanced against the holder to push the second portion over the first portion in order to fold the holder upon itself to secure the specimen in the holder, said slider thereafter being retractable away from said holder;
  means for spring loading said slider against said arm; and
  said means for securing being operable to release the holder.

15. The apparatus of claim 14, wherein said spring loading means further comprises a pushing member for folding the holder over on itself.

16. Apparatus for securing and transferring a specimen in a double folding grid having a lower grid, an upper grid hinged to the lower grid, said apparatus comprising:
  an elongate transfer arm having sides, an upper surface and a lower surface, a first end of said arm being mounted on a pivot;
  clip means spring mounted on said lower surface near a second end of said arm opposed to said first arm end, said clip means having a plurality of upstanding members, upper ends of said upstanding members extending above said upper surface, a clip portion being formed on each upper end and extending inwardly over said upper surface, said clip portions being spring loaded toward said upper surface;
  a bottom of said clip means operable to be pressed upwardly to raise said clip portions above said upper surface, wherein the lower grid may be placed on said upper surface in an open position, said clip bottom being releasable to secure the lower grid between said upper surface and said clip portions; and
  grid closing means slidably mounted on said arm and having an upper grid pushing member, said closing means slidable to contact the upper grid after the specimen has been loaded onto the lower surface of said grid, and then to fold the upper grid over the lower grid to secure the specimen therebetween, said closing means being slidably retractable toward said first arm end.

17. The apparatus of claim 16, wherein said arm is movable from a first location to a second location, said clip bottom being upwardly pressable in order to release the folded grid at the second location.

18. The apparatus of claim 17, wherein said transfer arm, said first location and said second location are all contained within a cryochamber.

19. The apparatus of claim 16, wherein:

said transfer arm pivot includes an upstanding handle coaxial with said pivot and is movable in a vertical axis, said second location having a block;

said handle operable to be pushed downwardly to press said arm downwardly against said block, said spring clip bottom being forced upwardly in order to raise said clip portions above said upper surface, said handle being raised in order to raise said arm above said location block in order to release said spring clip means, securing the grid to said upper arm surface, and said handle being twistable in order to pivot said transfer arm from the second location to the first location, said specimens being secured into said grid at said first workstation, said handle thereafter being twisted to move said arm from the first location to the second location, said handle being pushed downwardly in order to press said transfer arm onto said second workstation block, said spring clip bottom contacting said block and being pressed upwardly in order to raise said clip portions above said upper surface, said grid being released from said transfer arm at the second location.

20. The apparatus of claim 16, wherein said apparatus is adapted to transfer grids having dimensions less than four millimeters.

21. A method for securing at least one small specimen in a holder for use in connection with viewing under a microscope, comprising the steps of:

spring loading a spring clip mounted on an arm against an upper surface of the arm;

pressing the spring clip away from the upper surface in order to admit a lower portion of the holder between the upper surface and the spring clip;

releasing the spring clip to secure the lower portion to the upper surface;

placing at least one microscope specimen on the lower portion;

sliding a folder on the arm toward the holder until the folder contacts an upper portion of the holder hinged to the lower portion, the holder at this point being in an open position;

pushing the upper portion with the folder so that the upper portion folds over onto the lower portion, the holder then assuming a closed position; and slidably retracting the folder away from the holder.

22. Apparatus for securing a specimen in a specimen holder having a first portion and a second portion foldable on the first portion to secure said specimen in the holder, the apparatus comprising:

an arm including an upper surface and an opposed lower surface;

spring clip means mounted to said arm including a spring portion mounted to said lower surface, a plurality of upstanding clip portions extending upward from said spring portion to engage and be spring loaded against said upper surface, said spring clip means being operable to be pressed in an upward direction in order to space said clip portions above said upper surface to allow the introduction of the holder therebetween, said spring clip means being releasable to secure the holder between said clip portion and said upper surface; and a slider mounted on said arm and slidable between a position remote from the holder to a position proximate the holder, said slider operable to be advanced against the holder to push the second portion over onto the first portion, said slider thereafter being retractable away from said holder.

* * * * *